(12) United States Patent
Krause et al.

(10) Patent No.: US 7,863,480 B2
(45) Date of Patent: Jan. 4, 2011

(54) PROCESS FOR ALKALINE HYDROLYSIS OF CARBOXYLIC ACID DERIVATIVES TO CARBOXYLIC ACIDS

(75) Inventors: Eberhard Krause, Hohen Neuendorf (DE); Valentin Rohm, Munich (DE)

(73) Assignee: Krause-Rohm-Systems AG, Munich (DE)

( * ) Notice: Subject to any disclaimer, the term of this patent is extended or adjusted under 35 U.S.C. 154(b) by 192 days.

(21) Appl. No.: 12/302,125

(22) PCT Filed: Apr. 25, 2007

(86) PCT No.: PCT/EP2007/054061

§ 371 (c)(1), (2), (4) Date: Nov. 24, 2008

(87) PCT Pub. No.: WO2008/012118

PCT Pub. Date: Jan. 31, 2008

(65) Prior Publication Data

US 2009/0270649 A1    Oct. 29, 2009

(30) Foreign Application Priority Data

Jul. 28, 2006   (DE) .................. 10 2006 035 029

(51) Int. Cl.
*C07C 61/00* (2006.01)
*C07C 51/00* (2006.01)
*C01F 7/04* (2006.01)

(52) U.S. Cl. .............. 562/400; 462/483; 462/493; 462/512; 462/513; 462/590; 423/119; 423/121

(58) Field of Classification Search .............. None
See application file for complete search history.

(56) References Cited

U.S. PATENT DOCUMENTS 6,036,869 A * 3/2000 Selvarajan et al. .......... 210/733

FOREIGN PATENT DOCUMENTS

GB          652003 A       4/1951

OTHER PUBLICATIONS

Kurdwoski et al., Chapter 6- Red Mud and Phosphogypsum and their field of application, 1997, Waste materials used in concrete manufacturing, Noyes Publication, pp. 32.*

* cited by examiner

*Primary Examiner*—Jafar Parsa
*Assistant Examiner*—Yate' K Cutliff
(74) *Attorney, Agent, or Firm*—Barlow, Josephs & Holmes, Ltd.

(57) ABSTRACT

The invention relates to a process for alkaline hydrolysis of carboxylic acid derivatives, especially carboxylic esters, to carboxylic acids, wherein, for the alkaline hydrolysis of the carboxylic acid derivatives, red mud which is produced by the Bayer process used for aluminum production is used as a reaction-promoting component, especially as a hydroxide ion source.

23 Claims, 1 Drawing Sheet

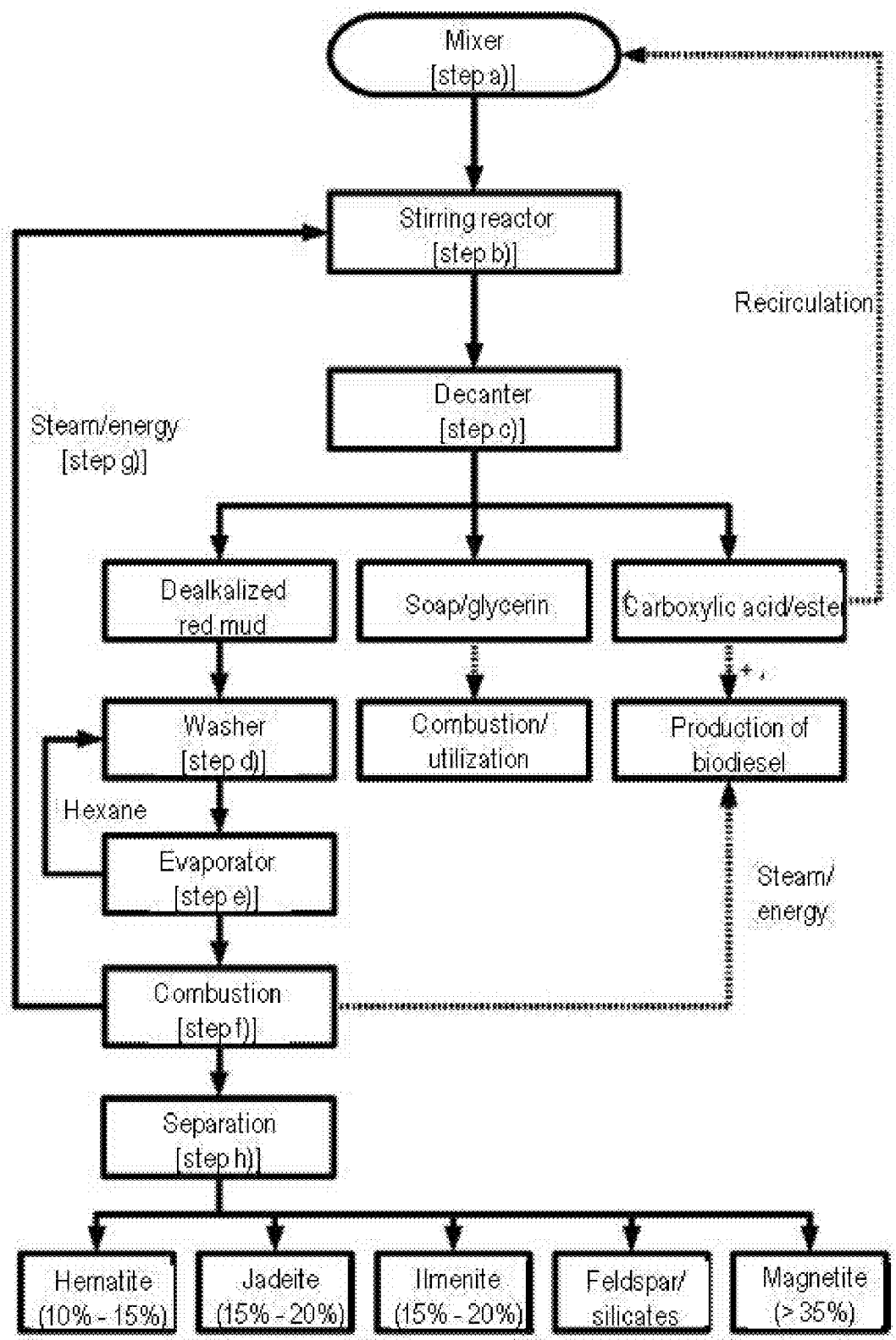
Figure

PROCESS FOR ALKALINE HYDROLYSIS OF CARBOXYLIC ACID DERIVATIVES TO CARBOXYLIC ACIDS

The invention relates to a method for alkaline hydrolysis of carboxylic acid derivatives to carboxylic acids.

BACKGROUND OF THE INVENTION

The carbonyl carbon atom of the carbonyl group of carboxylic acid derivatives is readily attacked by nucleophiles due to its positive partial charge. The arising addition intermediate product can again decompose by elimination of a leaving group. In this manner, it is possible to perform a substitution of the respective functional group in an addition elimination mechanism and to achieve mutual conversion of the various carboxylic acid derivatives. Therein, the reactivity of the carbonyl carbon greatly depends on the properties of the respective functional group. Therein, electron providing substituents with +I or +M effect, respectively, decrease the reactivity, electron drawing substituents with −I effect increase it. The following gradation of the carbonyl activity results from this, wherein only the most common carboxylic acid derivates are cited for clarity:

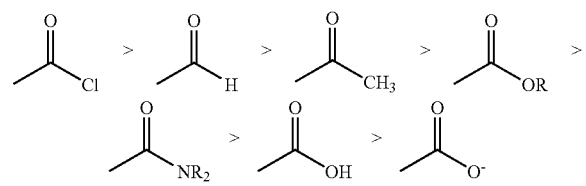

Since carboxylic acids or their deprotonated carboxylate ions, respectively, have the least carbonyl activity, as readily apparent, they can be obtained by alkaline hydrolysis from the remaining carboxylic acid derivates. Therein, the balance of these base-induced reactions usually is virtually completely on the side of the carboxylic acid or of the resonance-stabilized carboxylate ion deprotonated in a following step, respectively. Therein, the reaction proceeds according to the following general mechanism:

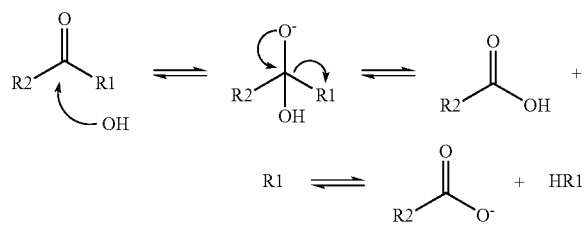

Therein, various variants for performing such reactions are known to the person skilled in the art from the prior art.

However, depending on the respective carboxylic acid derivative, multiple molar excess of hydroxide ions is required for performing such a reaction. Therein, the circumstance is to be regarded as disadvantageous in the known methods, that the required hydroxide ions mostly added in the form of sodium or potassium hydroxide are consumed during the reaction and present a comparatively high cost factor resulting in rise in cost of the method as well as of the corresponding products.

Therefore, the object of the present invention is to provide a more inexpensive method for alkaline hydrolysis of carboxylic acid derivatives to carboxylic acids.

BRIEF SUMMARY OF THE INVENTION

According to the invention, the object is solved by a method for alkaline hydrolysis of carboxylic acid derivatives to carboxylic acids having the features of claim 1. Advantageous developments with convenient and non-trivial developments of the invention are described in the further claims.

According to the invention, it is provided that red mud is used as a reaction-promoting component, especially as a hydroxide ion source, for the alkaline hydrolysis of carboxylic acid derivatives to carboxylic acids. Red mud is a mixture produced by the Bayer process used for obtaining aluminum. The Bayer process known per se and not concerned by the invention, therein, includes first release of $Al_2O_3$ from finely milled bauxite with the aid of caustic soda lye. After seeding with crystallization nuclei, pure $Al(OH)_3$ (gibbsite) is precipitated from the obtained sodium aluminate solution, which is electrolytically converted to metallic aluminum in further method steps. There remains a mixture which chemically considered is mainly composed of iron(III) oxides and hydroxides, titanium oxides, alumina residues, quartz sand, calcium oxide, sodium oxide as well as residual caustic soda lye, and is referred to as red mud due to its red color caused by iron(III) oxide. Therein, according to the quality of the used bauxite, 1 to 1.5 tons of red mud arise to each produced ton of aluminum as a non-avoidable attendant. The amount arising each year is several millions of tons and presents a serious environmental and disposal problem together with the already present waste of red mud. Therein, the main problem is the high alkalinity of the red mud due to its content of caustic soda lye with pH values between 11 and 13. At present, the disposal of the red mud is substantially effected by storage in sealed disposal sites, wherein the caustic soda lye exiting on the floor of the disposal site is collected and returned into the Bayer process. However, this form of storage and partial utilization is costly and expensive since large disposal site areas and plants are required, and high cost arise for the transport of the red mud and the caustic soda lye. Additionally, the long-term cost arising by the deposition can only hardly be calculated and present an additional economical problem.

A utilization of red mud as a reaction-promoting component within the scope of the method according to the invention for alkaline hydrolysis of carboxylic acid derivatives to carboxylic acids therefore offers very different advantages. Due to its high content of catalytically active components, the reaction is greatly accelerated by the addition of red mud, whereby an appreciable decrease of the method cost can be achieved. Additionally, red mud includes great amounts of caustic soda lye, and therefore it is an ideal source of the hydroxide ions required for performing the reaction at the same time. Since red mud is available worldwide in virtually unlimited amount and the alkaline components contained in the red mud present no cost factor but on the contrary the core of the problem, therefore, consumption of hydroxide ions during the reaction is particularly advantageous and desired in contrast to the prior art. Thus, the use of red mud within the scope of the method according to the invention offers both a dramatic decrease of the required material, method and disposal cost and an ecologically advantageous dealkalization of the red mud. At the same time, very different carboxylic acids can be produced from the corresponding carboxylic acid derivatives in particularly fast and inexpensive manner, wherein they can include all of the compound groups such as acid halides, aldehydes, ketones, acid anhydrides, esters, thioesters, amides or the like.

DETAIL DESCRIPTION OF THE INVENTION

In an advantageous development of the invention, the method according to the invention includes at least the steps of a) mixing the carboxylic acid derivative and the red mud, b) heating the mixture to a predetermined temperature value and/or mixing the mixture for the duration of a predetermined time at a predetermined pressure, and c) separating at least a first, especially liquid component from at least a second, especially amorphous component. In many cases, the alkaline hydrolysis is already started by mixing the educts such that it only has to be mixed for maintaining the reaction. However, depending on the respective carboxylic acid derivative, the reaction can proceed so slowly that additional or alternative heating of the mixture becomes required, respectively. In this manner, the required activation energy can be supplied to the reaction, and a conversion of the educts as quick and complete as possible can be achieved with extensive neutralization of the red mud. Therein, the duration of the reaction can be selected depending on the respective carboxylic acid derivative, the selected reaction conditions or the like. Therein, heating the mixture to about 98° C. over a duration of 2 hours has proven particularly economical for many reactions. However, it is to be noticed that these are only exemplary values and the invention is not limited thereto. For optimum adaptation of the reaction conditions to the respective facts, it can also be provided that the reaction is performed at increased pressure, for example in an autoclave, or at reduced pressure. After step b), in step c), separation of at least a first component from at least a second component is effected. Depending on the respective carboxylic acid derivative as well as the selected reaction conditions, one obtains further products corresponding to the respective leaving groups in addition to the corresponding carboxylic acids or carboxylates, respectively. Thus, for example, in use of thioesters besides carboxylic acids, the corresponding thiols develop, on the contrary, the use of carboxylic esters provides the corresponding alcohols. By separating at least a first, preferably liquid component from a at least a second, preferably amorphous and/or solid component, which especially includes dealkalized red mud, there is provided a simple manner for separating the heterogeneous reaction mixture into the respective products as well as for consideration of the respective aggregate states. Therein, the dealkalized red mud sediments in most cases within short time and forms an amorphous phase or suspension due to its small particle size, respectively, in which salts of the developed carboxylic acids can also be present. Therein, the red mud is simply identified by its intense red coloration. As also included within the scope of the invention, it is to be considered that further components and/or further phases are separated, for example to isolate additional solid or gaseous products, respectively. It can also be provided to separate non-converted educts and to reuse them in a further run of the method according to the invention.

In another advantageous development of the invention, it is provided that the carboxylic acid derivative includes at least a carboxylic ester. The alcohols formed of carboxylic esters in turn represent valuable compounds in addition to the obtainable carboxylic acids and are of great commercial interest. The use of a carboxylic ester therefore offers the possibility of obtaining plural valuable products in a single method and additionally to achieve dealkalization of the employed red mud.

In another advantageous development of the invention, it is provided that the carboxylic ester is a component of a vegetable oil, especially of a rape oil and/or palm oil and/or soya oil. Vegetable oils are mainly composed of mono-, di- and triglycerides and are available worldwide in great variety and in great amounts. Therein, basically, within the scope of the method according to the invention, each vegetable oil in each quality stage can be employed. Therein, palm oils, soya oils or rape oils offer particular advantages since they are inexpensive and globally available starting components and are to be appreciated as largely unproblematic under environmental aspects due to their biological degradability. However, the invention is not restricted to these sorts of vegetable oils. Since it is further not required within the scope of the method according to the invention to employ highly pure oils, additional cost can be saved by the use of unrefined, coarsely pressed or contaminated vegetable oils. In this manner, even waste products of the vegetable oil industry can be fed to advantageous utilization and also be used for obtaining carboxylic acids and further valuable products. It can also be provided to use the respective press cake or plant residues, respectively, instead of the pressed vegetable oils, since they also include residual amounts of carboxylic esters and moreover can also effect dealkalization of the red mud. Vegetable oils already have a certain amount of free fatty acids, by which a part of the alkaline red mud components is dealkalized already upon mixing. Therein, the corresponding salts of the fatty acids develop, which are referred to as soaps in this case. They can also quickly and simply be separated from the dealkalized red mud as commercially valuable components and be used for various purposes. Alternatively, the method according to the invention can also be used for changing a fatty acid pattern of the respective vegetable oil. A valuable product also developing by the alkaline hydrolysis is glycerin released from the glycerides contained in the vegetable oil. Glycerin, which for example finds use in the pharmaceutical and cosmetic industry as a valuable basic and raw material, can thus be inexpensively obtained in great amount by use of vegetable oils. All main and by-products of the method according to the invention can thus be commercially reused in use of vegetable oils, and additionally allow a particularly simple dealkalization and subsequent separation of the red mud with the commercial and ecological advantages associated therewith.

In another advantageous development of the invention, it is provided that water is additionally added in step a) and/or b). Thereby, optimum adaptation of the method to the respective educts and reaction conditions is possible. Therein, water can also be supplied to the reaction mixture in the form of vapor and be used both for heating and for mixing in step b).

In another advantageous development of the invention, it is provided that step c) includes at least a separating process, especially a density separating process and preferably a decanting process. Especially with regard to the large usability of the method according to the invention as well as the different educts and products, basically, therein, all of the separating processes common to the person skilled in the art are possible, with the aid of which separation of the developed product mixture in at least two components is achievable. Therein, besides thermal or chromatographic separating processes, especially density separating processes haven proven a suitable method in order to for example separate the dealkalized red mud present colloidal or amorphous, respectively, from another, for example liquid component. Therein, particularly decanting processes present a particularly simple, quick and inexpensive variant of the various density separating processes and offer an excellent separating power with low technical effort in the present case. However, it is to be emphasized that the invention is not restricted to density separating processes.

In another advantageous development of the invention, it is provided that the first component separated in step c) includes at least a carboxylic acid. The separated carboxylic or fatty acid, respectively, can thereby be fed to an economical utilization as a valuable product. Therein, for example, utilization as pure substance for the chemical industry, use as biologically degradable pest control agent in the agriculture or deprotonation to soaps can be provided. However, use as an educt for esterification reactions with short-chain alcohols for biodiesel production or the like is also conceivable.

In another advantageous development of the invention it is provided that the second component separated in step c) includes at least dealkalized red mud. The separated dealkalized red mud can be deposited without problem and without the necessity of expensive protective measures on the one hand, however offers very different possibilities for economically and ecologically advantageous further use on the other hand. Due to its high content of iron compounds it presents a particularly advantageous possibility of obtaining iron ore or of obtaining metallic iron, respectively, in its dealkalized form. Direct further use as iron providing component of an iron fertilizer utilizable in the agriculture is also conceivable. Furthermore, red mud includes various catalytically active compounds and can be used for example for dehydrogenation and dehydration of alcohols.

In another advantageous development of the invention, it is provided that step c) includes separation of a third component including at least a salt of a carboxylic acid. In this manner, there is provided an advantageous possibility to separate carboxylic acids or carboxylates, respectively, deprotonized during the method and thus present as soaps, and to recover them for example after acidification. However, direct use of the carboxylates for example as a detergent or the like is also conceivable.

In another advantageous development of the invention, it is provided that after step c), a further step d) is provided, which includes washing and/or extracting the second component with a solvent, especially a non-polar solvent. By such an additional step, there is provided a simple possibility of maximizing the product yield. Particularly in connection with separation of red mud as a second component, in this manner, driven or adhering, predominantly non-polar product residues can be separated from the highly polar red mud. Besides recovery of products, therein, of course, recovery of non-reacted educts is also conceivable, which can be advantageously reused upon new conduction of the method according to the invention.

In another advantageous development of the invention, it is provided that the solvent includes at least hexane. The use of hexane as a non-polar solvent therein offers the advantage that hexane is inexpensively available in great amounts, largely unproblematic in handing and again easily removable with a boiling temperature of 68° C. For performing the method, however, other non-polar solvents known to the person skilled in the art can also be provided.

In another advantageous development of the invention, it is provided that after step d) a further step e) is provided, which includes evaporation and/or recirculation of the solvent after step d). Therein, evaporation of the solvent presents a particularly simple possibility for separation thereof from the washed-out or extracted component, respectively. Additionally, the solvent can be used in a type of cycle process in an ecologically and economically particularly advantageous manner upon recirculation thereof after step d), and therefore the method according to the invention can be performed without appreciable consumption of solvent.

In another advantageous development of the invention, it is provided that after step c) and/or optionally d) and/or optionally e) a further step f) is provided, which includes at least partial oxidation and/or reduction, especially controlled combustion of the second component. Combustion under defined conditions for example including control of the oxygen supply, the selection of the oxidant or reductant, respectively, or the temperature control, provides utilizable thermal energy on the one hand and allows a particularly simple and inexpensive method for conversion of hematite contained in the red mud to magnetite in connection with dealkalized red mud as the second component on the other hand. For promoting or conducting the combustion, respectively, it can be provided to add natural or liquid gas to the red mud. Depending on the selected reaction conditions, additionally, synthesis gas, ethene or acetaldehyde can be obtained by this reaction, which in turn present important valuable products as central starting components of various chemical reactions. Therein, natural gas offers the advantage that it is virtually worldwide available in great amounts and allows a very inexpensive reaction conduction. The employment of natural gas additionally offers the advantage that the method can also be economically performed at remote natural gas deposits such as for example Alaska. Advantageously, the natural gas is additionally desulfurized during the method. However, admixture of wood, pulp, plant residues or the like is also conceivable in order to accomplish the combustion of the red mud.

In another advantageous development of the invention, it is provided that an exothermic reaction energy developing in step f) is used for evaporation of a liquid, especially water, in a further step g). Thereby, there is given another advantageous possibility for sustainable conduction of process and for comprehensive utilization of the developed thermal energy.

In another advantageous development of the invention, it is provided that the vapor produced in step g) is used for heating and/or mixing the reaction mixture in step b) and/or for generation of energy, especially by means of a gas/steam turbine. In this manner, the method can be performed virtually autonomous and independent of external sources of energy, which is particularly advantageous especially with regard to the often remote and hardly accessible red mud deposits. Additionally, thereby, the possibility of a continuous conduction of process is provided, since thermal energy arising during the method can be advantageously used in various method steps. Depending on the respective reaction conditions, in this manner, even excess of energy can be achieved, which can for example be used for operating other methods or for inputting into a power supply system.

In another advantageous development of the invention, it is provided that after step f) and/or optionally g) a further step h) is provided, which includes separation and/or division of solid reaction products developed in step f), particularly iron oxides. Therein, the separated iron oxides present valuable starting compounds for obtaining iron and are potent catalysts for a plurality of chemical reaction types.

In another advantageous development of the invention, it is provided that step h) includes separation and/or division of hematite and/or magnetite and/or jadeite and/or ilmenite and/or feldspar and/or silicates. Particularly the proportion of magnetite contained in the red mud can simply be separated from the remaining non-magnetic mineral components due to its ferromagnetic characteristics with the aid of magnetic separators and for example be further used for obtaining metallic iron. Separated jadeite can be returned into the Bayer process after its separation and be utilized for obtaining aluminum. The separated silicates are for example suited as admixture materials for the construction industry.

Further advantages, features and details of the invention are apparent from the following descriptions of several embodiments as well as by way of the drawing.

BRIEF DESCRIPTION OF THE DRAWING

Therein, the single FIG. 1 shows a schematic flow diagram of a preferred embodiment of the method.

EXAMPLE 1

Rape oil is mixed with red mud and water in a mixer (step a)) and pumped into a stirring reactor. In this context, it is of course conceivable that the respective reactants are considered and the pH value of the reaction mixture is adjusted to a respectively optimum value optionally by addition of water, acids or the like. The mixture is heated to about 98° C. in the stirring reactor and mixed for the duration of 2 hours (step b)). Therein, an alkaline hydrolysis of the glycerides contained in the rape oil to the corresponding carboxylic acids and glycerin is effected with the aid of the hydroxide ions contained in the red mud.

After completion of the reaction, the reaction mixture is transferred into a decanter (step c)), where it sediments within 30 minutes and forms various regions. Therein, they include an upper liquid phase with the developed fatty acids and non-reacted vegetable oil as well as a second underlying liquid phase with glycerin as well as the corresponding soaps of the fatty acids. On the bottom of the decanter, the dealkalized red mud settles in amorphous or suspended form, respectively. Due to the small particle size of the red mud, therein, complete separation into a solid and a liquid phase does not appear. By decanting, now, the upper liquid phase with carboxylic acids and residual vegetable oil is separated and divided into their individual components in a further step. Therein, the developed carboxylic acids can be used for production of biodiesel in an optional step after mixing with alcohol and catalyst in a manner known per se, while non-reacted vegetable oil can be returned into the mixer, reused in a new run of method or also be used for production of biodiesel. The subsequently decanted second phase with glycerin and the corresponding soaps of the fatty acids can in turn be separated in another optional step and be utilized or be combusted for obtaining energy, respectively.

Caused by the small particle size and the great surface associated therewith, the sedimented dealkalized red mud contains both non-reacted reaction educts and non-separated reaction products. For maximizing yield, in the present example, it is transferred into a washer (step d)) and washed with hexane. In this manner, the residual non-polar or predominantly non-polar compounds, respectively, such as glycerin, fatty acids or esters can be separated as far as possible from the highly polar dealkalized red mud and be recovered. Optionally, the washing step can be repeated multiple times therein. The hexane is separated together with the non-polar or predominantly non-polar compounds dissolved in it, respectively, extracted or distilled from them in a further method step in an evaporator (step e)) from it, respectively, and returned into the washer. In this manner, the hexane can circulate largely lossless and in operational cost decreasing manner in a closed cycle. Instead of hexane, other non-polar solvents such as pentane, heptane or toluene can also be used therein, wherein the inventive idea is not restricted to these compounds.

The washed dealkalized red mud is transferred into a further reactor and combusted with supply of natural gas (step f)). Therein, it can also be provided to combust (step f)) the dealkalized red mud directly after decanting (step c)) without one or more additional washing steps (step f)). The air supply of the combustion is preferably controlled such that the reaction proceeds under sub-stoichiometric conditions. This allows reduction of the hematite ($Fe_2O_3$) contained in the red mud to magnetite ($Fe_3O_4$). The end of the reaction can be determined in particularly simple manner by the color change of the red mud from red ($Fe_2O_3$) to black ($Fe_3O_4$). The thermal energy developing in combustion can optionally be used for evaporating water. The developed water vapor can either be utilized for obtaining energy by means of a gas/steam turbine or be returned into the stirring reactor for heating and mixing the reaction mixture (step g)). In this manner, the entire method can be performed continuously, largely without external energy supply and with overall positive energy balance. It can also be provided to use the energy released upon combustion in further methods such as the production of biodiesel, the Bayer process or the like.

After completion of the combustion, the solid residue is separated, milled and decomposed into magnetic iron ore and a low-iron residual mineral stock with the aid of a magnetic separator (step h)). Therein, the low-iron residual mineral stock can be further separated in a manner known per se, thereby especially obtaining residual hematite, jadeite, ilmenite, feldspar and silicates. With at least 90%, the concentration of pure magnetite in the separated iron ore is about two times as high as in qualitatively high-grade natural ore. In methods known per se, iron can be obtained from the separated iron ore, while the low-iron residual mineral stock for example finds use as a cement addition material. Thereby, the method according to the invention provides various valuable products such as glycerin, soaps and iron ore in addition to carboxylic acids, and therefore offers a comprehensive utilization of the various red mud components.

EXAMPLE 2

Alkaline Hydrolysis of Carboxylic Esters

In a reaction vessel with stirrer and reflux condenser, 200 g of red mud are mixed with 100 g of 2-methylbutanoic acid ethyl ester, wherein the red mud has a residual water content above 10%. Optionally, the mixture can be diluted with water or an inert solvent as far as mixing without problem is ensured. In use of liquid carboxylic esters, they basically can also be added in excess and thereby function as a solvent themselves. The mixture is stirred at room temperature for about 2 hours with stirring, wherein the 2-methylbutanoic acid ethyl ester saponifies to 2-methylbutanoic acid and ethanol. Optionally, towards the end of the reaction time, the reaction temperature can be increased and the mixture be boiled at reflux in order to ensure a conversion as complete as possible. After cooling, the mixture is filtered and the liquid phase is extracted plural times with hexane. The combined organic phases are subsequently dried over calcium chloride and the hexane is subsequently extracted at the rotary evaporator for recovery. The remaining liquid phase can optionally be further cleaned by distillation.

EXAMPLE 3

Alkaline Hydrolysis of Carboxylic Chlorides

In a reaction vessel with reflux condenser, drying tube and dropping funnel, 5 g of red mud are mixed with 20 g of pyridine. With stirring, about 2 g of benzoyl chloride are carefully added in drops. After occurred addition, the mixture is heated on the water bath for 10 minutes. Alternatively, it can also be stirred at room temperature for 1 hour. After cooling, one adds ice water and filtrates the mixture through a glass frit, wherein the dealkalized red mud contained in the amorphous filter cake is post-washed with ice water. Alternatively, the dealkalized red mud can also be separated from the liquid phase by sedimentation and subsequent decantation. Subsequently, the filtrate is acidified with concentrated hydrochloric acid and three times extracted with ether. The combined ethereal phases are sequentially washed with saturated sodium hydrogen carbonate and saturated sodium chloride solution and dried over sodium sulfate. Finally, it is filtrated and optionally the obtained benzoic acid is recrystallized after extracting the solvent.

EXAMPLE 4

Alkaline Hydrolysis of Carboxylic Anhydrides

In a reaction vessel with reflux condenser, drying tube and dropping funnel, 20 g of red mud is mixed with as much water as reliable mixing is ensured. With vigorous stirring, one adds about 5 g of maleic anhydride in drops. After occurred addition, the mixture is heated on the water bath for 20 minutes and poured into ice water after cooling. The dealkalized red mud is sucked through a glass frit and washed with ice water. The liquid phase is processed in known manner in order to obtain the product maleic acid.

EXAMPLE 5

Alkaline Hydrolysis of Carboxylic Acid Amides 50 g of red mud are suspended with 200 ml of triethylene glycol and mixed with 10 g of tridecan acid amide. The mixture is boiled at reflux for about 4 hours with stirring until development of ammonia is no longer observed. After cooling, one adds 300 ml water and acidifies the mixture with 20% sulfuric acid. After sedimentation of the red mud, the precipitated tridecan acid is removed, washed with water and optionally cleaned by recrystallization. For maximizing yield, the red mud is shaken out with hexane and the hexane is subsequently extracted in vacuum after drying over sodium sulfate.

EXAMPLE 6

Alkaline Hydrolysis of Vegetable Oil

Red mud is mixed with Water and Vegetable Oil in a High-Pressure Reactor. Rape oil, soya oil or palm oil can for example be used as the vegetable oil. Subsequently, the mixture is heated to a temperature of about 250° C. for 2 hours at a pressure of 50 bar, thereby hydrolyzing the vegetable oil to free carboxylic acids and glycerin. The carboxylic acids ascend during the reaction and can be removed there.

EXAMPLE 7

Alkaline Hydrolysis of Thioesters 10 g of red mud are mixed with 50 ml of water. Subsequently, 5 g of cyclohexyl thioacetate are dropped thereto and stirred at room temperature for 30 min. After processing the mixture in known manner, dealkalized red mud, acetic acid and cyclohexanethiol can be isolated as products.

The invention claimed is:
1. Method for alkaline hydrolysis of carboxylic acid derivatives, wherein the carboxylic acid derivatives are carboxylic esters, to carboxylic acids, comprising
adding red mud produced by a process consisting of the Bayer process used for production of aluminum as the hydroxide ion source, for alkaline hydrolysis of the carboxylic acid derivatives.
2. Method according to claim 1, characterized by the following steps:
a) mixing the carboxylic acid derivative and the red mud;
b) heating the mixture to a predetermined temperature value and/or mixing the mixture for the duration of a predetermined time at a predetermined pressure; and
c) separating at least a first, liquid component from at least a second, amorphous component.
3. Method according to claim 1, characterized in that the carboxylic acid derivative includes at least a carboxylic ester.
4. Method according to claim 3, characterized in that the carboxylic ester is a component of a vegetable oil.
5. Method according to claim 2, characterized in that in step a) and/or b) water is additionally added.
6. Method according to claim 2, characterized in that step c) includes at least a separating process.
7. Method according to claim 2, characterized in that the first component separated in step c) includes at least a carboxylic acid.
8. Method according to claims 2, characterized in that the second component separated in step c) includes at least dealkalized red mud.
9. Method according to claim 2, characterized in that step c) includes separation of a third component including at least a salt of a carboxylic acid.
10. Method according to claim 2, characterized in that after step c), a further step d) is provided, which includes washing and/or extracting the second component with a solvent.
11. Method according to claim 10, characterized in that the solvent includes at least hexane.
12. Method according to claim 10, characterized in that after step d) another step e) is provided, which includes evaporation and/or recirculation of the solvent after step d).
13. Method according to claim 2, characterized in that after step c) and/or optionally d) and/or optionally e), a further step f) is provided, which includes at least partial oxidation and/or reduction, and wherein the at least partial oxidation and/or reduction is controlled combustion of the second component.
14. Method according to claim 13, characterized in that an exothermic reaction energy developing in step f) is used for evaporation of a liquid in a further step g).
15. Method according to claim 14, characterized in that the vapor generated in step g) is used for heating and/or mixing of the reaction mixture in step b) and/or for generation of energy.
16. Method according to claim 13, characterized in that after step f) and/or optionally g) a further step h) is provided, which includes separation and/or division of solid reaction products developed in step f).
17. Method according to claim 16, characterized in that step h) includes separation and/or division of hematite and/or magnetite and/or jadeite and/or ilmenite and/or feldspar and/or silicates.
18. The method according to claim 4, wherein the vegetable oil is a rape oil and/or palm oil and/or soya oil.

19. The method according to claim 6, wherein the separating process is a decanting process.

20. The method according to claim 7, wherein the carboxylic acid is a fatty acid.

21. The method according to claim 10, wherein the solvent is a non-polar solvent.

22. The method according to claim 14, wherein the liquid is water.

23. The method according to claim 15, wherein the energy is generated by means of a gas/steam turbine.

\* \* \* \* \*